United States Patent

West

Patent Number: 5,962,737
Date of Patent: *Oct. 5, 1999

[54] 2-AMINO-1-PHENYLPROPANOLS, STEREOSPECIFIC SYNTHESIS THEREOF, AND METHOD OF OPTICALLY RESOLVING THE SAME

[76] Inventor: Daniel David West, 1 Warren Ct., Rockport, Mass. 01966

[*] Notice: This patent issued on a continued prosecution application filed under 37 CFR 1.53(d), and is subject to the twenty year patent term provisions of 35 U.S.C. 154(a)(2).

[21] Appl. No.: 08/780,573

[22] Filed: Jan. 8, 1997

[51] Int. Cl.⁶ ................................. C07C 209/88
[52] U.S. Cl. .................. 564/304; 549/437; 549/443; 564/361; 564/364; 568/306
[58] Field of Search ................... 564/361, 364, 564/304; 549/437, 443; 514/466, 653; 568/306

[56] References Cited

U.S. PATENT DOCUMENTS

| | | | |
|---|---|---|---|
| 1,948,162 | 2/1934 | Bockmuhl et al. | 564/358 |
| 1,951,302 | 3/1934 | Bockmuhl et al. | 564/364 |
| 1,964,973 | 7/1934 | Bockmuhl et al. | 564/362 |
| 1,995,709 | 3/1935 | Hartung | 564/358 |
| 2,083,001 | 6/1937 | Bockmuhl et al. | 564/361 |
| 2,151,459 | 3/1939 | Bockmuhl et al. | 564/361 |
| 2,359,707 | 10/1944 | Baltzly et al. | 564/358 |
| 3,775,479 | 11/1973 | Bruderer et al. | 564/265 |
| 3,804,834 | 4/1974 | Mentrup et al. | 564/362 |
| 4,237,304 | 12/1980 | Dowd et al. | 548/239 |

*Primary Examiner*—Richard L. Raymond
*Attorney, Agent, or Firm*—Evelyn M. Sommer

[57] ABSTRACT

Stereospecific synthesis of the racemic threo isomers of 2-nitro-1-phenylpropanols by reacting a benzaldehyde derivative with nitroalkane in the presence of a tertiary amine and reducing 2-nitro-1-phenylpropanols with, for example, lithium aluminum hydride to 2-amino-1-phenylpropanols is described. Also described are phase transfer resolution of racemic mixtures of 2-amino-1-phenylpropanol and its derivatives into their optically pure isomers by reacting a racemic mixture with the mono alkali metal salt of a tartaric acid ester in a two phase system of a hydrocarbon and water. The specification further describes therapeutically useful optically pure isomers of threo-2-amino-1-(dialkoxy or alkoxy) phenylpropanols and acid addition salts thereof.

12 Claims, No Drawings

2-AMINO-1-PHENYLPROPANOLS, STEREOSPECIFIC SYNTHESIS THEREOF, AND METHOD OF OPTICALLY RESOLVING THE SAME

BACKGROUND

1. Field of Invention

This invention relates to improved processes for the production of isomers and derivatives of 2-amino-1-phenylpropanol, their isolation and the use of derivatives of D-threo-2-amino-1-propanol as therapeutic sympathomimetic agents. These agents can be successfully used in treating obesity, depression, and other conditions.

BACKGROUND

2. Discussion of Prior Art

Sympathomimetic agents have long been used in medicine for their effects on the blood vessels and the peripheral and central nervous system. The present invention relates to compounds having their effect primarily on the central nervous system which are derivatives of β-phenethylamine.

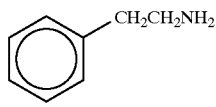

One such compound is the alpha methyl derivative commonly known as amphetamine.

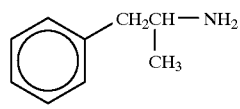

Amphetamines are important therapeutic compounds that have been widely used for many years in the form of various salts, isomers and derivatives thereof. Specifically, amphetamines have been used as appetite suppressants to treat obesity, as CNS stimulants to treat depression and other psychogenic disorders, in the treatment of narcolepsy, epilepsy, post-encephalitic parkinsonism, and hyperkinetic syndromes in children who suffer from minimal brain disfunction.

However, amphetamines are disfavored, partly due to their short-lived effectiveness (tolerance), but more because of the considerable abuse potential (addiction).

There is a great need for an effective appetite suppressing agent that is free from abuse liability and development of tolerance as obesity remains a challenging problem because of its increasingly understood linkage to other serious disorders.

Amphetamine and its derivatives undergo a number of metabolic transformations catalyzed by enzymes in vivo. The presence of the alpha methyl group retards the rate of deamination by monoamine oxidase (MAO) enzymes and allows the transformation shown below to occur:

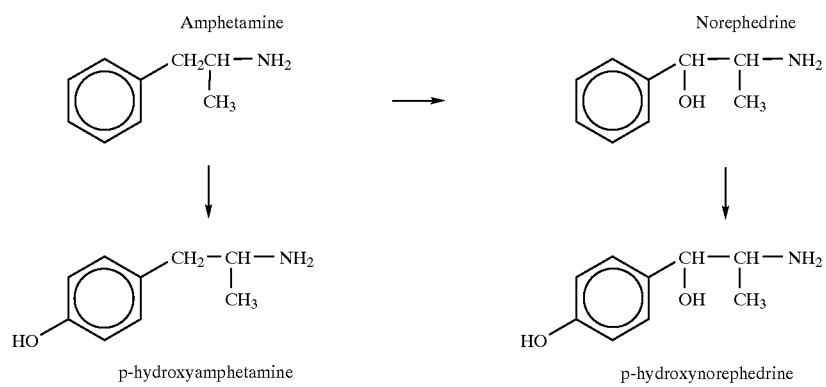

The upper right compound—norephedrine—has proven to be relatively free of abuse liability and tolerance development, while still retaining some of the appetite suppressing properties of amphetamine. A racemic mixture of norephedrine - phenylpropanolamine (PPA)—has a somewhat stronger appetite suppressing effect than optically pure norephedrine due to the presence of the D-isomer. Phenylpropanolamine (PPA) has been widely used in non-prescription appetite suppressants.

Among the diasteromers, the D-isomer of norephedrine - D-pseudonorephedrine—has the greatest appetite suppressing effect, approaching that of amphetamine. Moreover, the D-isomer is relatively free of abuse and tolerance development. This compound has been marketed mostly in Europe under the names "Adiposetten" and "Amorphen" by the German companies, Reiss and Heumann, respectively. D-pseudonorephedrine occurs in nature in the leaves of the Kat plant, Catha Edulis Forsk, and Celastraceae (an evergreen shrub native to southern Arabia and Ethiopia). It is also found in smaller amounts in the South American tree Maytenus Krukonii A. C. Smith Celastraceae, and in the mother liquor from Ma Huang after the recovery of ephedrine.

All of the above compounds (including ephedrine itself) are not entirely free from undesirable sympathomimetic agent side effects. The above compounds can produce nervousness, insomnia, dizziness, restlessness, anxiety, tremors, hyperactive reflexes, and later weakness, fatigue, and general depression.

Cardiovascular effects may result in headache, hypothermia, tachycardia, arrhythmia, anginial pain, and sweating. Gastrointestinal effects may include dry mouth and nasal passages, metallic taste, nausea and vomiting, and diarrhea with abdominal cramps. In addition, chronic use may produce a form of paranoid psychosis. These compounds are generally contraindicated in cases of hypertension, heart disease, diabetes, kidney disease, and thyroid disorder.

In an effort to overcome some of these drawbacks, a considerable amount of research was carried out by Cook and Fellows of SmithKline who filed numerous patents including British patent No. 828,880 and U.S. Pat. No. 2,974,148 (1961), describing the use of isomers of methylenedioxyamphetamine (MDA) as ataractic and anorexigenic agents. While these compounds did eliminate many of the previously encountered side effects, MDA proved to have an abuse liability equal to amphetamine and was included in the Controlled Substance Act of 1970.

The following table summarizes the pharmaceutical uses of 2-amino-1-phenylpropanols derivatives based on the following structural formula:

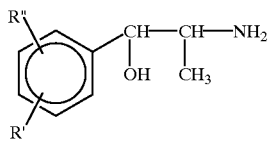

TABLE 1

Derivatives of 2-amino-1-phenylpropanol

| Phenyl-propanolamine | R' | R" | Stereo-chemistry | Indication | Prod. Name |
|---|---|---|---|---|---|
| (DL-Norephedrine) | H | H | DL-erythro | sympatho-mimetic | Propadrine |
| L-Norephedrine | H | H | L-erythro | sympatho-mimetic | |
| D-Norpseudo ephedrine | H | H | D-threo | appetite suppressant | Adiposetten |
| Metaraminol | H | 3-OH | L-erythro | sympatho-mimetic | Aramine |
| p-Hydroxy norephedrine | H | 4-OH | D-L erythro | sympatho-mimetic | |
| Corbadrine | 3-OH | 4-OH | L-erythro | vaso-constrictor | Corefrine |
| Methoxamine | 2-OCH₃ | 5-OCH₃ | D,L-erythro | vaso-constrictor | Vasylox |

The compounds shown in Table I possess two asymmetric carbon atoms and exist as threo and erythro diastereoisomers. In addition, the threo and erythro forms each exist as D and L enantiomers, for a total of four possible stereoisomeric forms as shown in Table B below:

| | | Configuration Activity* | C1 | C2 | Relative Pressor |
|---|---|---|---|---|---|
| $\begin{array}{c} CH_3 \\ H\ 2\ NH_2 \\ O\ 1\ OH \\ C_6H_5 \end{array}$ | $\begin{array}{c} CH_3 \\ H\ 2\ NH_2 \\ HO\ 1\ H \\ C_6H_5 \end{array}$ | L erythro | S | S | 1.0 |
| | | D erythro | R | S | 0.33 |
| | | D threo | S | S | 0.2 |
| | | L threo | R | R | depressor |

*Relative to ephedrine.

The four stereo isomers, in general, produce different pharmacological responses.

Thus, the threo forms and the D isomers tend to be more centrally active while the erythro forms and the L isomers tend to be more vasoactive. For example, the threo form of racemic 2-amino-1-phenylpropanol is active as an appetite suppressant [the D threo form (Adiposatten) is more active], but relatively weak as a vasoconstrictor or bronchial dilator. In contrast, the erythro form (Propadrine) and its L enantiomer (L-Norephedrine) exhibit powerful vasoconstrictor activity.

While some of the optical isomers have been separated, it is usually difficult and costly to do so. Moreover, mechanisms to prepare the optically pure isomers have not been available.

Mixed stereoisomers of 2-amino-1-phenylpropanol can be readily prepared by reacting benzaldehyde with nitroethane in the presence of an alkaline catalyst to produce 2-nitro-1-phenylpropanol which is then reduced to the amine. E.g., Hoover and Hass, *Journal of Organic Chemistry*, 12, 506, (1947). This reaction gives excellent yields at low cost. However, separating the stereoisomers produced by this reaction has not been satisfactory. As a result, heretofore, the only practical stereospecific synthesis of 2-amino-1-phenylpropanols involves the reduction of propiophenone derivatives to the racemic erythro diastereoisomers and fractional crystallization of the amine salt of an optically active acid.

The DL-erythro forms can be readily obtained from the appropriate propiophenone derivatives or by inversion of DL-threo derivatives. Since the pharmacological properties of the D and L isomers differ, it is desirable to separate the two, resulting in maximum therapeutic utility. While such potentially useful products can also be prepared, the difficulty of separating, i.e. "resolution", the isomers has prevented their development.

Specifically, the base is converted to a salt of an optically active acid. For example, the DL-base is reacted with a D-acid. This results in the formation of a mixture of D-base-D-acid and L-base-D-acid. These two salts differ in solubility. When the mixture is cooled and allowed to stand, the D-base-D-acid, typically being the less soluble, precipitates out of the solution first. By removing the precipitate at the appropriate time, the collected precipitate is largely the D-base-D-acid, while the L-base-D-acid remains in solution.

While this results in purification of the optical isomers to some extent, substantial impurities often remain. These impurities are removed to some degree by fractional crystallization. The "pure" D and L bases are then liberated by adding a sufficient amount of an alkali to a solution of the "pure" salt to produce a pH above 7.

The above process is very tedious, time consuming, and inefficient. In addition, a base with the same configuration as the resolving acid is more easily separated and purified than the opposite enantiomer. Consequently, in practice, the desired isomeric base must be matched with an optically active acid of the same configuration to achieve maximum yields.

OBJECTS AND ADVANTAGES

Accordingly, the objects and advantages of the improved processes for stereospecific synthesis and optical resolution, include providing a simple, efficient and less costly process for producing optically pure isomers of 2-amino-1-phenylpropanols and their derivatives.

Additionally, the present invention provides a less tedious method of resolving the optical isomeric forms of derivatives of D-threo-2-amino-1-propanol and therefore provides these compounds at a lower cost.

Furthermore, products of the present invention, namely the optically pure derivatives of D-threo-2-amino-1-propanol function as therapeutic sympathomimetic agents which:

(a) have a lower tolerance development in the human body;

(b) are less likely to be abused; and (c) have fewer side effects.

As a result, the present invention provides safe and effective alternative treatments for obesity, depression or other psychogenic disorders, narcolepsy, epilepsy, postencephalitic parkinsonism and hyperkinetic syndromes in children who suffer from minimal brain dysfunction, as well as numerous other disorders.

DESCRIPTION OF INVENTION

It has been discovered that if a benzaldehyde derivative is reacted with a nitroalkane in the presence of a tertiary amine, the nitroalcohol formed is of a threo configuration rather than a mixture of threo and erythro isomers which results when sodium hydroxide is used as the catalyst. The mechanisms of these reactions are shown below.

$R_X$—C$_6$H$_4$—CHO + RCH$_2$NO$_2$ $\xrightarrow{\text{NaOH}}$ threo and erythro $R_X$—C$_6$H$_4$—CH(OH)—CHR(NO$_2$)

$R_X$—C$_6$H$_4$—CHO + RCH$_2$NO$_2$ $\xrightarrow{R_3N}$

-continued threo alone $R_X$—C$_6$H$_4$—CH(OH)—CHR(NO$_2$)

Benzaldehyde derivatives that will react according to this invention include: benzaldehyde and benzaldehydes containing halogen, hydroxy, alkyl and alkoxy groups, and combinations thereof, in the aromatic ring.

The nitro alkane can be nitroethane or nitropropane. The tertiary amines include trimethylamine, triethylamine, tributylamine, and others (R=alkyl).

The reaction is best conducted in an aqueous aliphatic alcohol.

The tertiary amine employed must be free of primary and secondary amines which interfere with the reaction. These can be removed from the commercial products by refluxing with acetic or phthalic anhydride followed by distillation.

In a preferred embodiment of the synthetic method of the present invention, a benzaldehyde derivative is reacted with nitroethane in the presence of triethylamine in aqueous ethanol. The mixture is allowed to react at room temperature for twenty-four hours. The mixture is then acidified with an organic acid since mineral acids tend to promote decomposition, as does heat. Excess solvents and reactants are evaporated and the nitroalcohol extracted.

The nitroalcohol can easily be reduced by catalytic hydrogenation or conventional reducing agents such as zinc and acid. Lithium aluminum hydride has been found to work exceptionally well. The racemic threo isomers can readily be inverted to the racemic erythro isomers by reaction with acetic anhydride and thionyl chloride and hydrolysis. N-methyl derivatives can be prepared by adding an equimolecular amount of aqueous formaldehyde to the primary amine and reducing the Schiff base The use of a primary aliphatic alkylamine results in the formation of the dehydration product of the nitroalcohol—the beta-nitrostyrene. By employing a secondary or tertiary amine in the presence of water, nitrostyrene formation is completely eliminated. The use of a secondary or tertiary amine prevents the formation of a Schiff base amine, the necessary intermediary for nitrostyrene formation.

$R_X$—C$_6$H$_4$—CHO + RNH$_2$ $\longrightarrow$ $R_X$—C$_6$H$_4$—CH=NR + H$_2$O $R_X$—C$_6$H$_4$—CH=NR + RCH$_2$NO$_2$ $\longrightarrow$ -continued

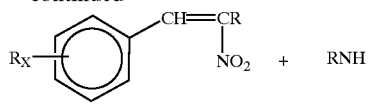

While the use of either the secondary or tertiary amine prevents nitrostyrene formation, only the tertiary amine results in stereospecificity.

The racemic threo isomer can readily be inverted to the racemic erythro isomers by reaction with acetic anhydride and thionyl chloride and hydrolysis.

N-methyl derivatives, such as those listed in Table 1, can be prepared by adding an equimolecular amount of aqueous formaldehyde to the primary amine and reducing the Schiff base catalytically.

Instead of the usual fractional crystallization of the amine-acid salt, the method of resolving stereo isomers of the present invention uses a novel phase transfer resolution. It has been discovered that if the amine base is rapidly stirred with a mono alkali metal salt "of" a tartaric acid ester in a two-phase system of a hydrocarbon and water, a rapid and efficient resolution can be achieved.

The amine bases which can be used in accordance with this invention are represented by the following formula:

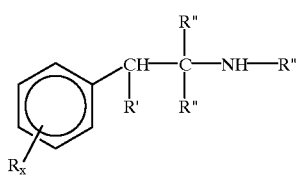

wherein R'=H, OH, or alkoxy; R"=H, or alkyl; R'''=H, OH, or alkyl; x=1–5 and $R_x$=H, halogen, hydroxy, alkyl, alkoxy groups, and combinations thereof. In a preferred embodiment of the present invention, at least one of $R_x$ is not H.

Sodium and potassium are each useful as the alkali metal of the alkali metal salt. Useful tartaric acid esters include dibenzoyl and ditoluoyl tartrate. Useful hydrocarbon phases may be aromatic (benzene, toluene, etc.) or halogenated aliphatic (dichloromethane, dichloroethane, etc.).

In a practical embodiment of the resolution method of the present invention, a DL-2-amino-1-phenylpropanol derivative in dichloromethane is combined and stirred with dibenzoltartaric acid in water, and aqueous sodium hydroxide for from about one to three hours. The reaction mixture is then allowed to stand for the about same length of time. The dichloromethane phase is separated and dried over anhydrous magnesium sulfate. Evaporation gives the L-threo isomer in nearly quantitative yield. The aqueous phase is made alkaline with ammonia and extracted with dichloromethane. The dichloromethane extract is dried over anhydrous magnesium sulfate and evaporated to give the D-threo isomer in nearly quantitative yield.

Amphetamine has alpha and beta stimulant sympathomimetic activities and enhances the turnover rate of both norepinephrine and dopamine while depleting norepinephrine centrally.

The side effects of amphetamine and related compounds are mainly due to excessive beta receptor stimulation. Methamphetamine, for example, being a stronger beta stimulant than amphetamine, produces more pronounced cardiovascular effects. On the other hand, amphetamine has less beta activity than racemic amphetamine and causes fewer cardiovascular side effects.

The addition of a beta-hydroxy group to amphetamine reduces abuse liability and tolerance development, but does not reduce cardiovascular beta effects. Among the four possible isomers L-2-amino-1-phenylpropanol, the D threo isomer, has the greatest alpha/beta ratio and results in the fewest side effects.

In accordance with this invention it has been discovered that the nuclear substitution of certain alkoxy or alkoxy alkyl groups to D-threo-2-amino-1-phenylpropanol results in an optimum alpha/beta ratio while still maintaining a minimal abuse liability and tolerance development. These compounds may be used advantageously as substitutes for amphetamine as they are a series of novel sympathomimetic agents with amphetamine-like activity, but having fewer side effects than PPA or the like, and little or no abuse liability and tolerance development.

These derivatives of D-threo-2-amino-1-phenylpropanol have the structure shown below:

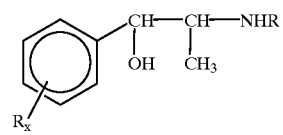

$R_{x,x=1-5}$=H, halogen, hydroxy, alkyl, alkoxy groups such as methoxy, acetals, methyl, etc., and combinations thereof.

The alkoxy or alkoxy alkyl D-threo-2-amino-1-phenylpropanol are prepared by reacting an appropriately substituted benzaldehyde derivative with nitroethane in the presence of an alkaline catalyst and reducing the formed nitroalcohol. The resulting DL-threo aminoalcohol may then be resolved into the D-threo and L-threo isomers. Although the D isomers have the highest therapeutic index, the L and DL forms are not without pharmacological activity and are included within the scope of this invention.

The hydrochloride salts are preferably used in this invention, however any non-toxic pharmaceutically acceptable acid addition salts or the freebase itself may be employed. Examples of salts that may be used include the sulfate, phosphate, nitrate, citrate, acetate, lactate, tartrate, and benzoate. The salts are readily prepared by reacting the freebase with a stoichiometric amount of the desired acid in a suitable solvent such as ethanol, ether, ethyl acetate, acetone, water, or various combinations of solvents.

For example, hydrochloride salts of the bases can be prepared by dissolving the free base (about 1 mole) in anhydrous ether (500 ml.) and bubbling dry hydrogen chloride gas through the solution until the precipitation is completed. The hydrochloride salt precipitate is filtered with suction and dried. The salt is recrystallized from aqueous isopropanol.

The products of this invention may be administered in all conventional pharmaceutical forms including tablets, hard and soft gelatin capsules, and elixirs, each compounded using conventional procedures. The capsules are prepared containing 5, 10 or 15 mg of an active component and are administered depending on the content as 1 to 3 capsules per day. The tablets generally contain 5 mg of an active component and are administered similarly to the capsules. Solutions are formulated so that 5 ml of solution contains 5 mg of the active component and are administered in amounts of 5 to 15 ml per day depending on the condition of the recipient subject.

The following examples will serve to illustrate, but not limit the scope of this invention:

EXAMPLE 1

A racemic mixture of threo nitroalcohols was prepared by combining freshly distilled benzaldehyde (1 mole), nitroethane (2.5 moles), and triethylamine (0.05 mole) in ethanol (150 ml.) with water (75 ml.). This mixture was allowed to stand at room temperature in the dark for twenty-four hours. The mixture was then ice-cooled and acetic acid (0.05 mole) was added to the reaction mixture. Alcohol and excess nitroethane were evaporated (vacuum). Water (75 ml.) was added and the nitro alcohol extracted with ethyl acetate, dried over anhydrous sodium sulfate and the solvent evaporated (vacuum) to give the product, a viscous oil (yield 70–80% based on the benzaldehyde). GC/MS and NMR data were consistent with proposed structures. NMR indicates pure threo isomer on the basis of the coupling constant of the benzylic proton [—OCH-doublet J=9.4 Hz (formic acid)].

EXAMPLE 2

The nitro alcohols were reduced by two methods, a zinc and acid method and a lithium aluminum hydride method as described below:

(A) Zinc and Acid

Hydrochloric acid (4 moles) is added (with stirring) to a mixture of nitroalcohol (1 mole), zinc dust (4 moles), and 400 ml. of 95% ethanol. The acid is added at such a rate that the temperature remains at 45 degrees or below (several hours are usually required). Stirring is continued for 1–2 hours after completing the addition. The acid solution is extracted with ether to remove non-basic materials. Excess NaOH solution is then added and the free base extracted with ether. The ether solution is dried (MgSO$_4$) evaporated, and the product distilled or crystallized in the usual manner (70–80% yield).

(B) Lithium Aluminum Hydride ("LAH")

A solution of the nitroalcohol (1 mole) in tetrahydrofuran (400 ml.) is added to a solution of lithium aluminum hydride (4 moles) in tetrahydrofuran (500 ml.) with rapid stirring and cooling (as necessary) to maintain gentle reflux. After the addition is complete, the mixture is refluxed for an additional 2 hours.

Water is added to neutralize excess LAH (1 liter) and the product extracted with benzene. The benzene extract is dried (MgSO$_4$) and the benzene evaporated. The resulting product is purified by either distillation or crystallization (80–90% yield).

EXAMPLE 3

The reaction mixture of reduced nitro alcohols was resolved into optically pure isomers by the following process.

A mixture of a DL-threo-2-amino-1-phenylpropanol (1 mole) in dichloromethane (600 ml.), dibenzoyltartaric acid (0.5 mole) in distilled water (30 ml.), and sodium hydroxide (0.5 mole) in distilled water (50 ml.) is stirred rapidly for two hours and allowed to stand for two hours. The dichloromethane phase is separated using a separating funnel over anhydrous magnesium sulfate. Rotary evaporation of the dichloromethane phase gives the L-threo isomer in nearly quantitative yield.

The aqueous phase is made alkaline with ammonia to pH 13 and extracted with dichloromethane. The dichloromethane extract is dried over anhydrous magnesium sulfate and evaporated to give the D-threo isomer in nearly quantitative yield. The enantiomeric purity of the products is 96–99% based on GLC analysis of the D or L-α-methoxy-α-trifluromethylphenylacetamide (MTPA) derivatives.

EXAMPLE 4

The method of the present invention was used to prepare optically pure D-threo-2-amino-1-phenylpropanol and its hydrochloride salt. These products had the following properties:

Base m.p. 75–77° C. $[\alpha]^{25}_D$+37.3° (c=2, E+OH)

HCl m.p. 179–181° C. $[\alpha]^{25}_D$+42.5° (c=2, H$_2$O)

Enantiometric purity; 99% by glc.

EXAMPLE 5

The method of the present invention was used to prepare optically pure D-threo-2-amino-1-(3,4-dimethoxy) phenylpropanol and its hydrochloride salt. These products had the following properties:

Base m.p. 132–133° C. $[\alpha]^{25}_D$+33–50 (c=2, E+OH)

HCl m.p. 160–162° C. $[\alpha]^{25}_D$+38.2° (c=2, H$_2$O) Enantiometric purity; 99% by glc.

EXAMPLE 6

The method of the present invention was used to prepare optically pure D-threo-2-amino-1-(3,4-methylenedioxy) phenylpropanol and its hydrochloride salt. These products had the following properties:

Base m.p. 86–88° C. $[\alpha]^{25}_D$+42.8° (c=2, E+OH)

HCl m.p. 210–212° C. $[\alpha]^{25}_D$+48.8° (c=2, H$_2$O)

Enantiometric purity; 99% by glc.

EXAMPLE 7

The method of the present invention was used to prepare optically pure D-threo-2-amino-1-(2,5 dimethoxy) phenylpropanol and its hydrochloride salt. These products had the following properties:

Base m.p. 134–136° C. $[\alpha]^{25}_D$31.3(c=2, E+OH)

HCl m.p. 163–165° C. $[\alpha]^{25}_D$33.7(c=2, H$_2$O)

Enantiometric purity; 96% by glc.

EXAMPLE 8

The method of the present invention was used to prepare optically pure D-threo-2-amino-1-(3,4,5-trimethoxy) phenylpropanol and its hydrochloride salt. These products had the following properties:

Base m.p. 193–195° C. $[\alpha]^{25}_D$28.5(c=2, E+OH)

HCl m.p. 235–237° C. $[\alpha]^{25}_D$29.1(c=2, H$_2$O)

Enantiometric purity; 96% by glc.

The use of the isomers and derivatives of threo-2-amino-1-propanol as therapeutic sympathomimetic agents as delineated in this invention will serve to provide a safe and effective treatment for obesity, depression and other psychogenic disorders, narcolepsy, epilepsy, postencephalitic parkinsonism, and hyperkinetic syndromes in children who suffer from minimal brain dysfunction, as well as numerous other disorders.

The present invention provides a simplified processes to more efficiently, and at less cost, produce optically pure isomers and derivatives of 2-amino-1-phenylpropanol as well as means of using such compounds as therapeutic agents.

The scope of the invention should be determined by the appended claims and their legal equivalents, rather than by the examples given.

What I claim is:

1. A stereospecific synthesis of threo isomers of 2-nitro-1-phenylpropanols having the formula

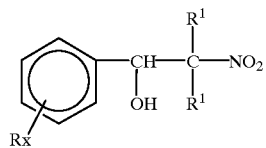

wherein R is member selected from the group consisting of hydrogen, hydroxy, halogen, alkyl and alkoxy, x has a value of from 1 to 5 and R' is a member selected from the group consisting of hydrogen and alkyl which comprises reacting a benzaldehyde with a nitroalkane in the presence of a tertiary amine.

2. The synthesis of claim 1 in which said nitroalkane is a member of the group consisting of nitroethane and nitropropane.

3. The synthesis of claim 1 in which said tertiary amine is an aliphatic tertiary amine.

4. The synthesis of claim 3 in which said aliphatic tertiary amine is at least one member of the group consisting of trimethyl amine, triethyl amine, tripropyl amine, tri-isopropyl amine, tri-butyl amine, trisobutylamine and tri-tertbutyl amine.

5. The synthesis of claim 1 further comprising the step of reducing the 2-nitro-1-phenylpropanol formed to a 2-amino-1 phenylpropanol.

6. The synthesis of claim 5 in which said reducing is conducted using a reducing agent selected from a group consisting of (a) zinc and an acid, and (b) lithium aluminum hydride.

7. The process of resolving a racemic mixture of 2-amino-1 phenylpropanols having the formula

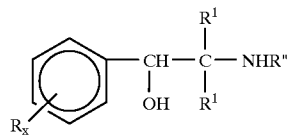

wherein R is member selected from the group consisting of hydrogen, hydroxy, halogen, alkyl and alkoxy, x has a value of from 1 to 5, R' is member selected from the group consisting of hydrogen and alkyl and R" is member selected from the group consisting of hydrogen and alkyl and alkoxy, into its optical isomers comprising reacting said racemic mixture with a mono alkali metal salt of a tartaric ester in a biphasic hydrocarbon water system.

8. The resolution process of claim 7 in which said alkali metal of said alkali metal salt is selected from a group consisting of lithium, sodium, potassium and combinations thereof.

9. The resolution process of claim 7 in which said tartaric acid ester is selected from the group consisting of dibenzoyl, ditoluoyl tartrate and combinations thereof.

10. The resolution process of claim 7 in which said hydrocarbon phase is selected from the group consisting of aromatic hydrocarbons, aliphatic hydrocarbons, halogenated aliphatic hydrocarbons and combinations thereof.

11. The resolution process of claim 10 in which said aromatic hydrocarbon is selected from the group consisting of benzene, toluene, xylene and combinations thereof.

12. The resolution process of claim 10 in which said halogenated aliphatic hydrocarbon is selected from the group consisting of methylene chloride, dichloroethane and combinations thereof.

* * * * *